(12) United States Patent
Che et al.

(10) Patent No.: US 8,772,485 B2
(45) Date of Patent: Jul. 8, 2014

(54) PALLADIUM COMPLEXES FOR ORGANIC LIGHT-EMITTING DIODES

(71) Applicants: Chi Ming Che, Hong Kong (CN); Chi Fai Kui, Hong Kong (CN); Pui Keong Chow, Yuen Long (CN)

(72) Inventors: Chi Ming Che, Hong Kong (CN); Chi Fai Kui, Hong Kong (CN); Pui Keong Chow, Yuen Long (CN)

(73) Assignee: The University of Hong Kong, Hong Kong (HK)

( * ) Notice: Subject to any disclaimer, the term of this patent is extended or adjusted under 35 U.S.C. 154(b) by 0 days.

(21) Appl. No.: 13/682,035

(22) Filed: Nov. 20, 2012

(65) Prior Publication Data

US 2013/0150580 A1     Jun. 13, 2013

Related U.S. Application Data

(60) Provisional application No. 61/569,184, filed on Dec. 9, 2011.

(51) Int. Cl.
*H01L 51/00* (2006.01)

(52) U.S. Cl.
USPC ............................................................. 546/4

(58) Field of Classification Search
None
See application file for complete search history.

(56) References Cited

U.S. PATENT DOCUMENTS

2006/0134461 A1 * 6/2006 Huo et al. ...................... 428/690
2011/0095281 A1 * 4/2011 Parham et al. .................. 257/40
2012/0018711 A1 * 1/2012 Che et al. ........................ 257/40

* cited by examiner

*Primary Examiner* — Janet L Andres
*Assistant Examiner* — Timothy R Rozof
(74) *Attorney, Agent, or Firm* — Amin, Turocy & Watson, LLP

(57) ABSTRACT

Subject matter disclosed herein relates to a series of palladium based materials, their preparation method and their applications in an organic light-emitting diode (OLED).

20 Claims, 18 Drawing Sheets

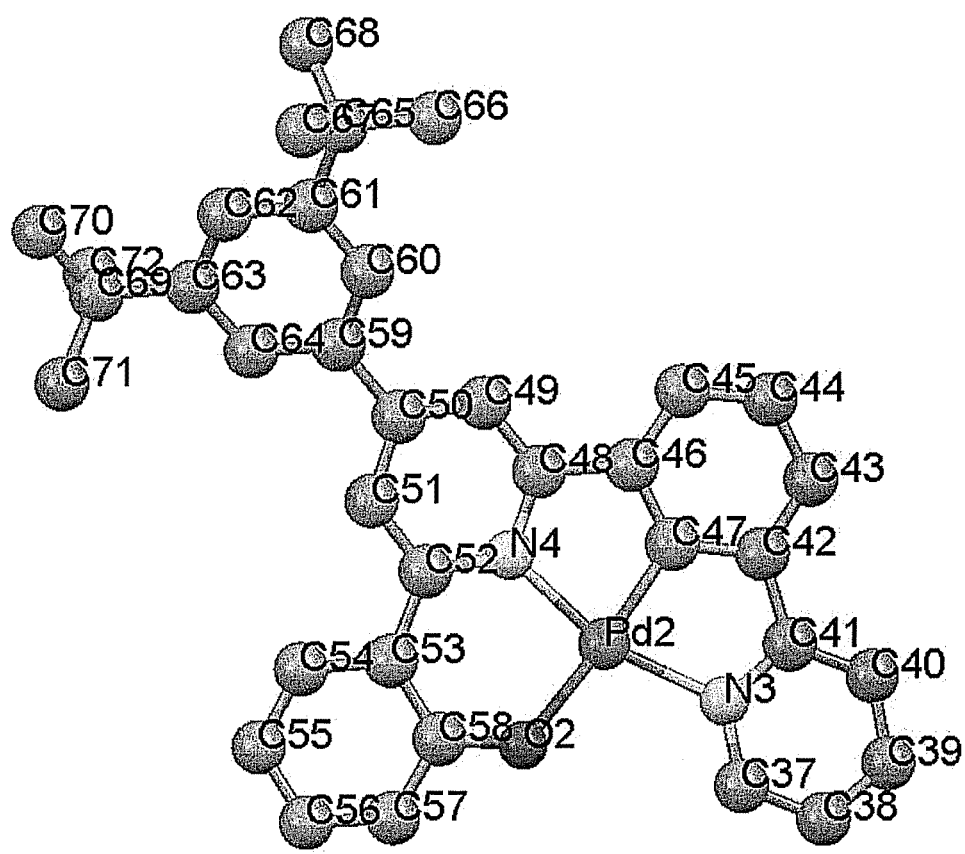
Figure 1: X-ray crystal structure of Complex 101

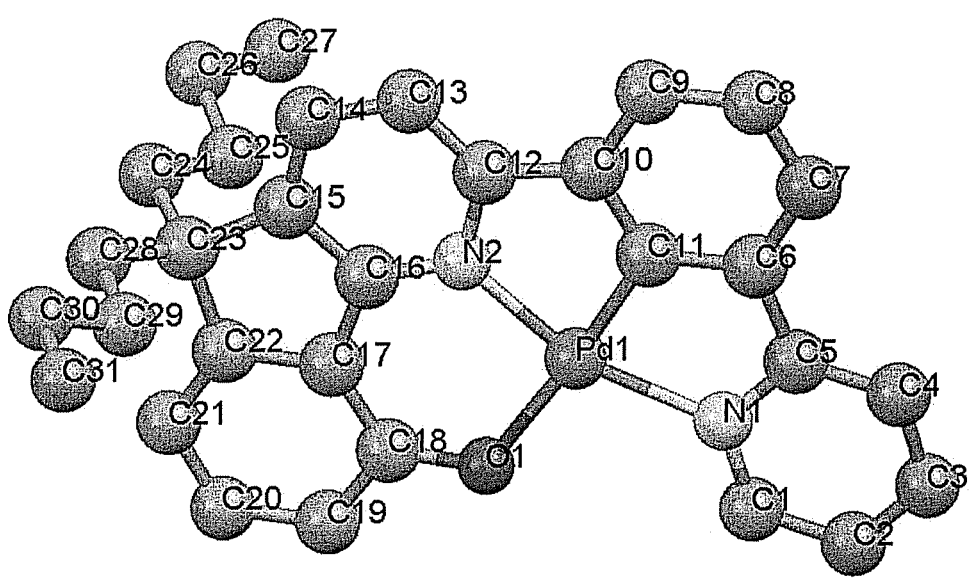
Figure 2: X-ray of Complex 104

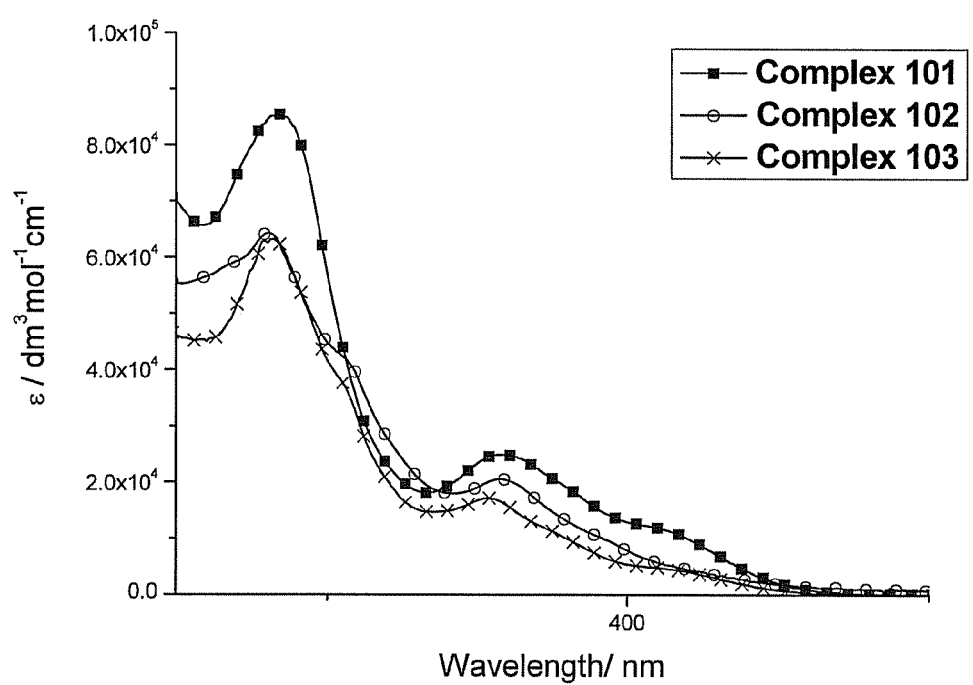
Figure 3: UV-visible spectrum of complexes 101–103 in $CH_2Cl_2$ solution.

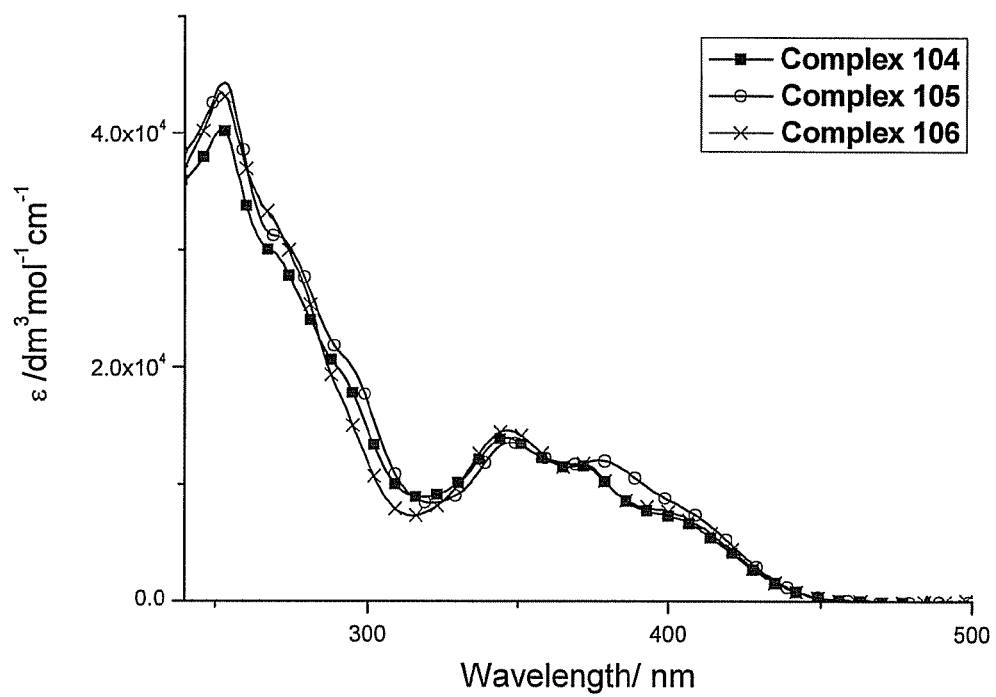
Figure 4: UV-visible spectrum of complexes 104–106 in $CH_2Cl_2$ solution.

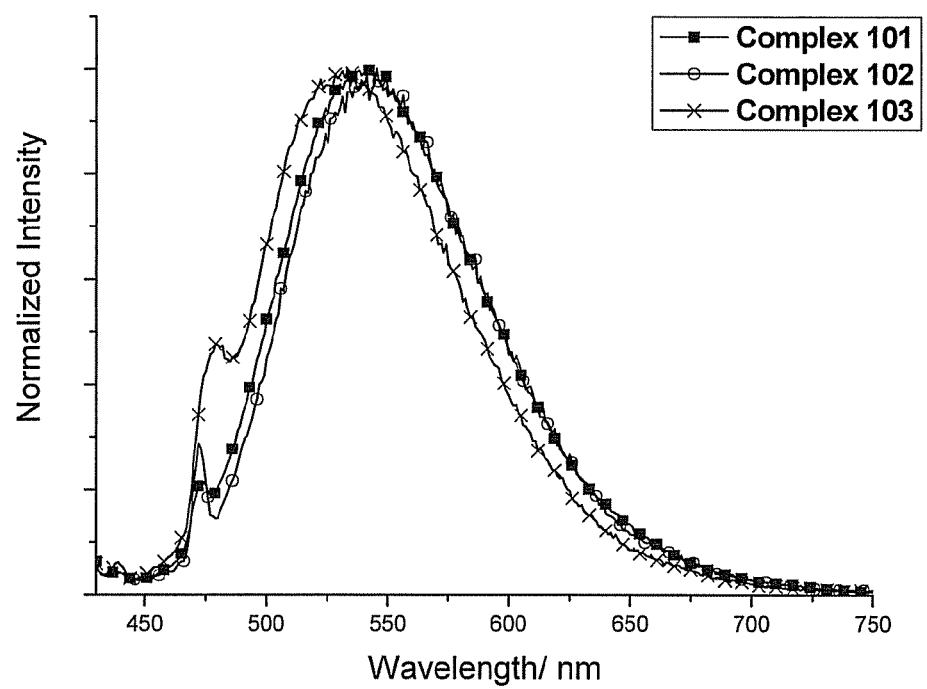
Figure 5: Photoluminescent spectra of complexes 101–103 in CH$_2$Cl$_2$ solution.

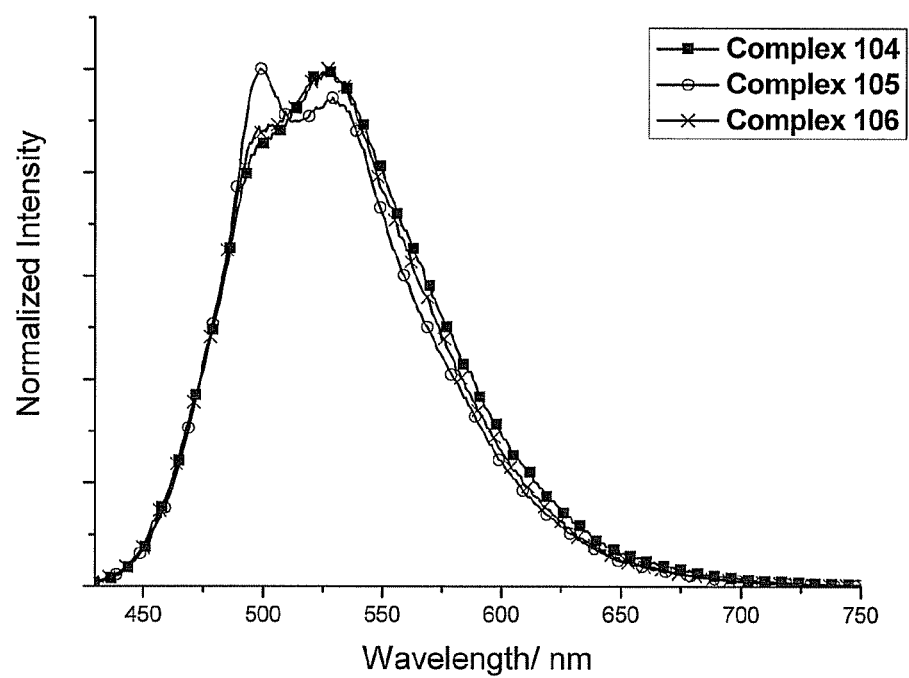
Figure 6: Photoluminescent spectra of complexes 104–106 in $CH_2Cl_2$ solution.

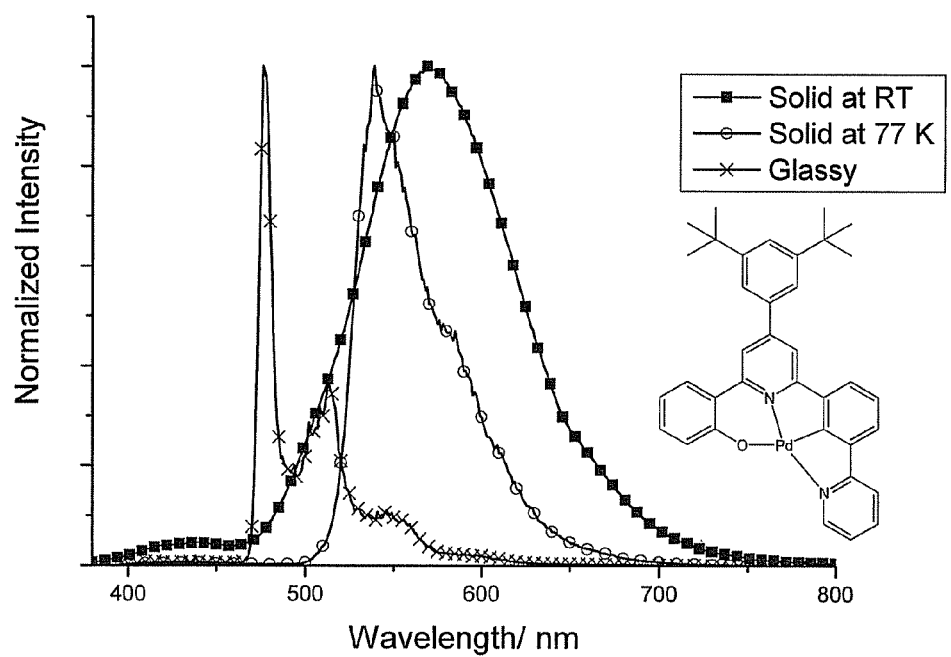
Figure 7: Solid-state (298 K), Solid-state (77 K) and Glassy (77 K) photoluminescent spectra for Complex 101

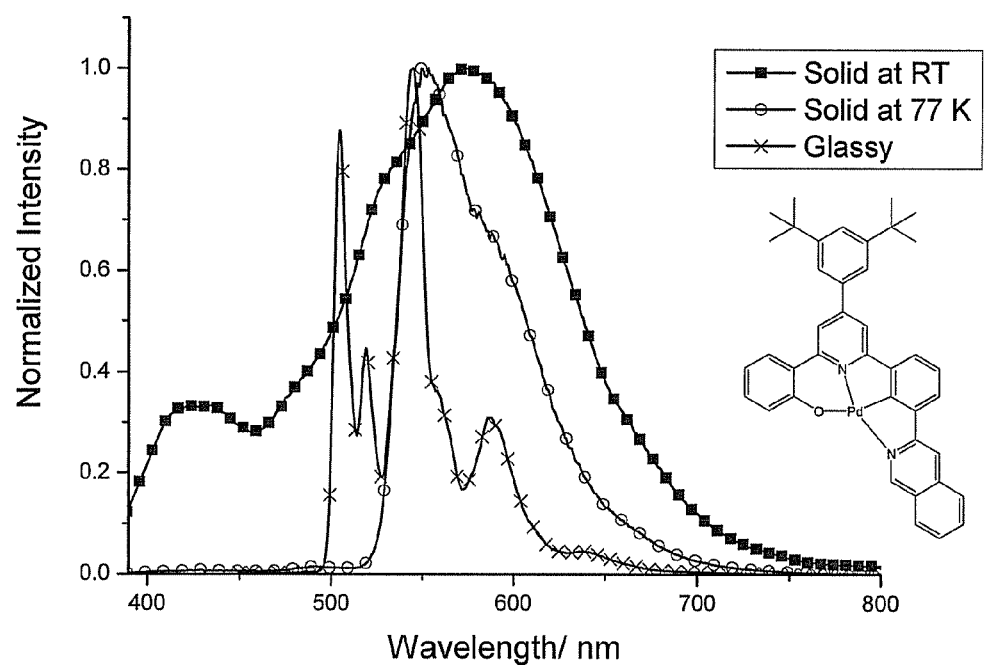
Figure 8: Solid-state (298 K), Solid-state (77 K) and Glassy (77 K) photoluminescent spectra for Complex 102

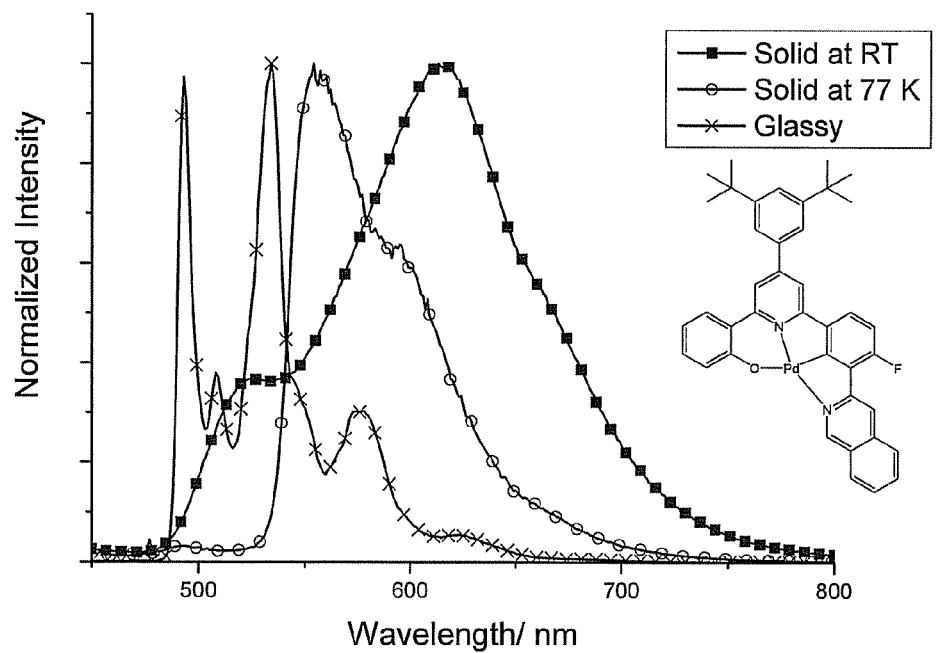
Figure 9: Solid-state (298 K), Solid-state (77 K) and Glassy (77 K) photoluminescent spectra for Complex 103

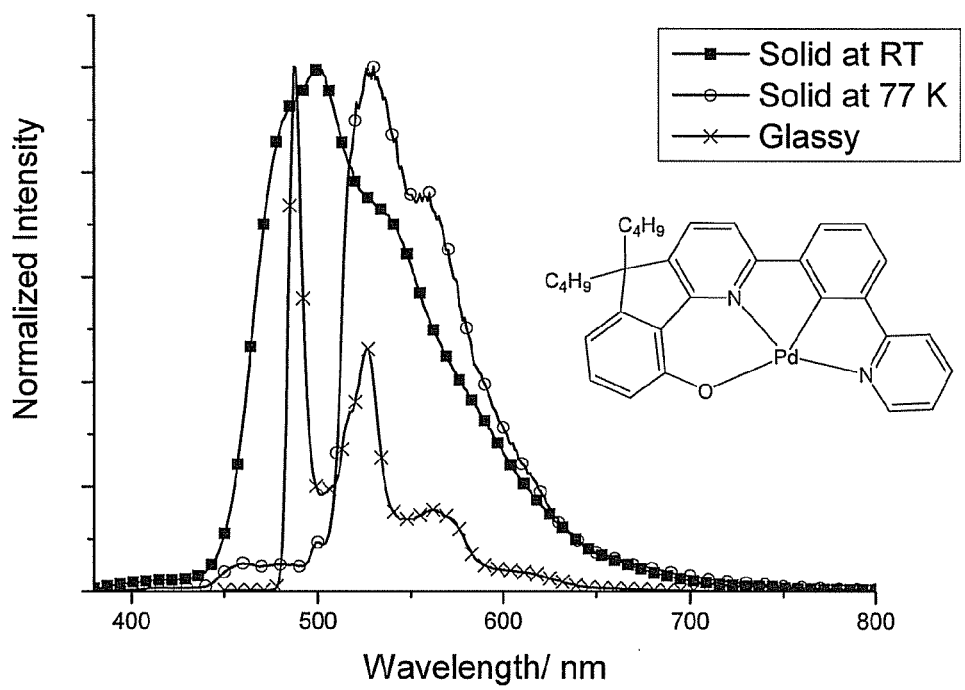
Figure 10: Solid-state (298 K), Solid-state (77 K) and Glassy (77 K) photoluminescent spectra for Complex 104

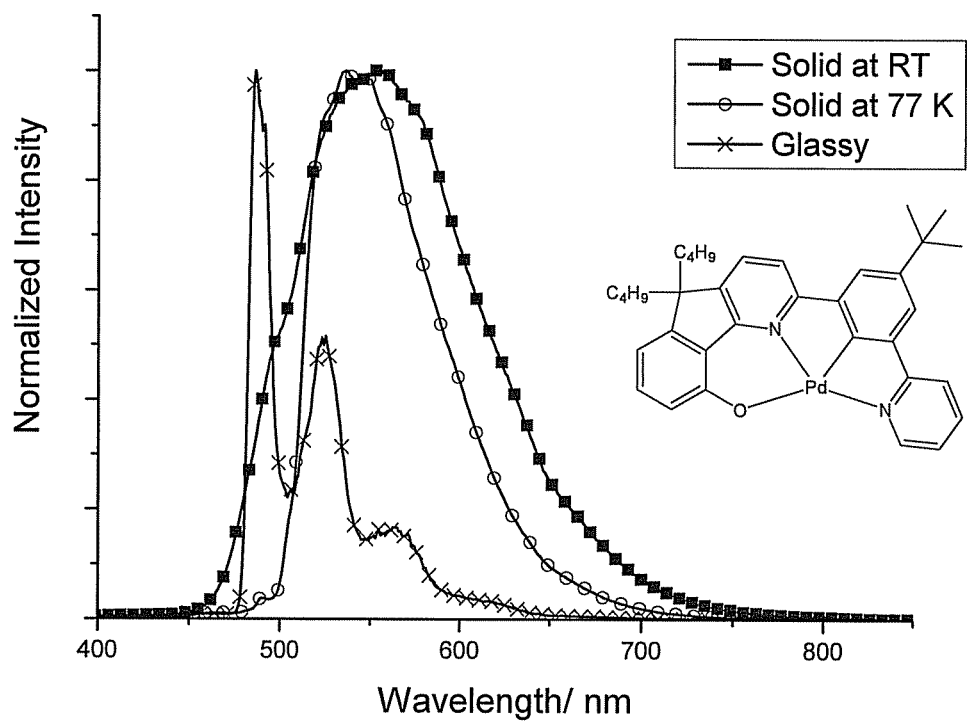
Figure 11: Solid-state (298 K), Solid-state (77 K) and Glassy (77 K) photoluminescent spectra for Complex 105

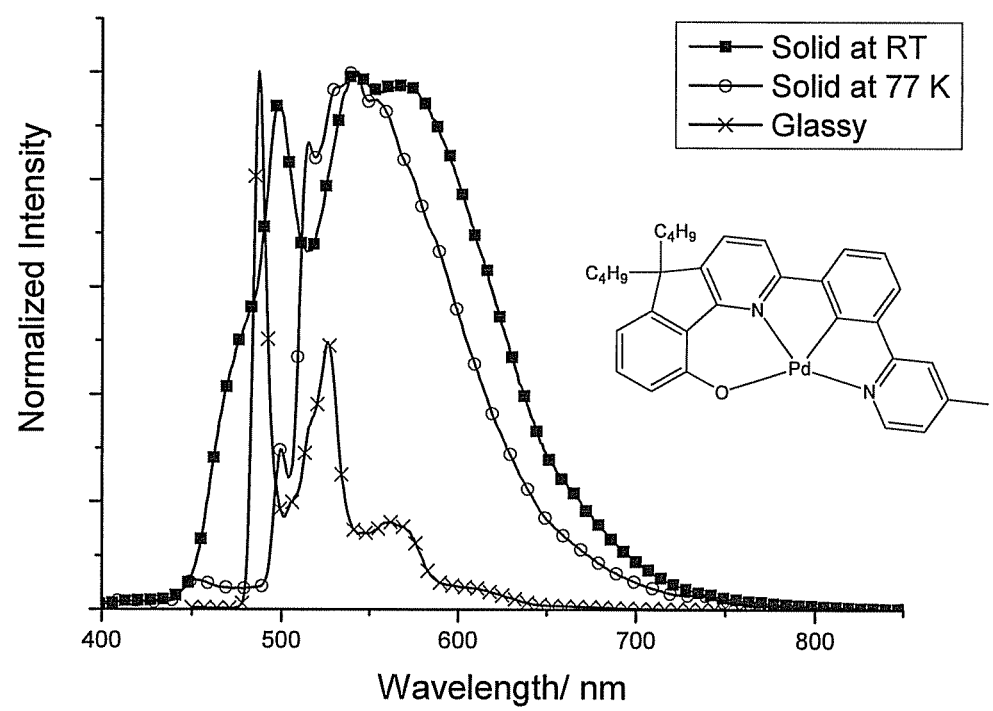
Figure 12: Solid-state (298 K), Solid-state (77 K) and Glassy (77 K) photoluminescent spectra for Complex 106

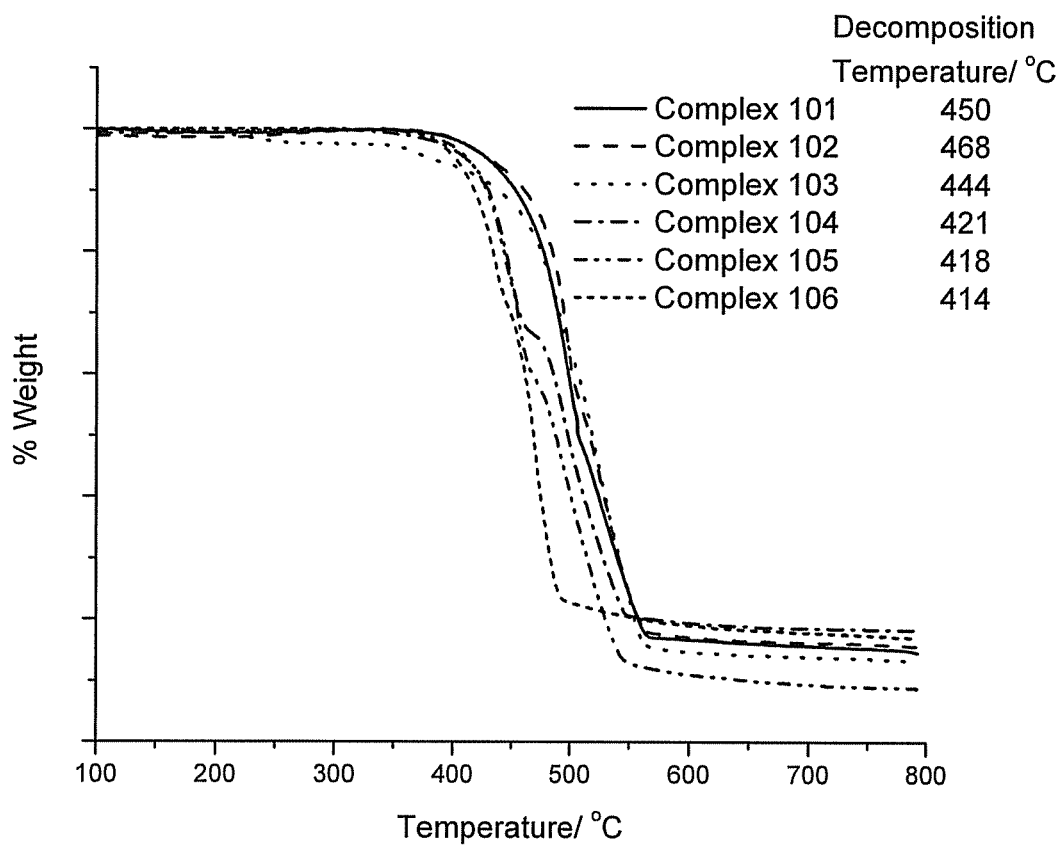
Figure 13: Theromgrams for complexes 101–106.

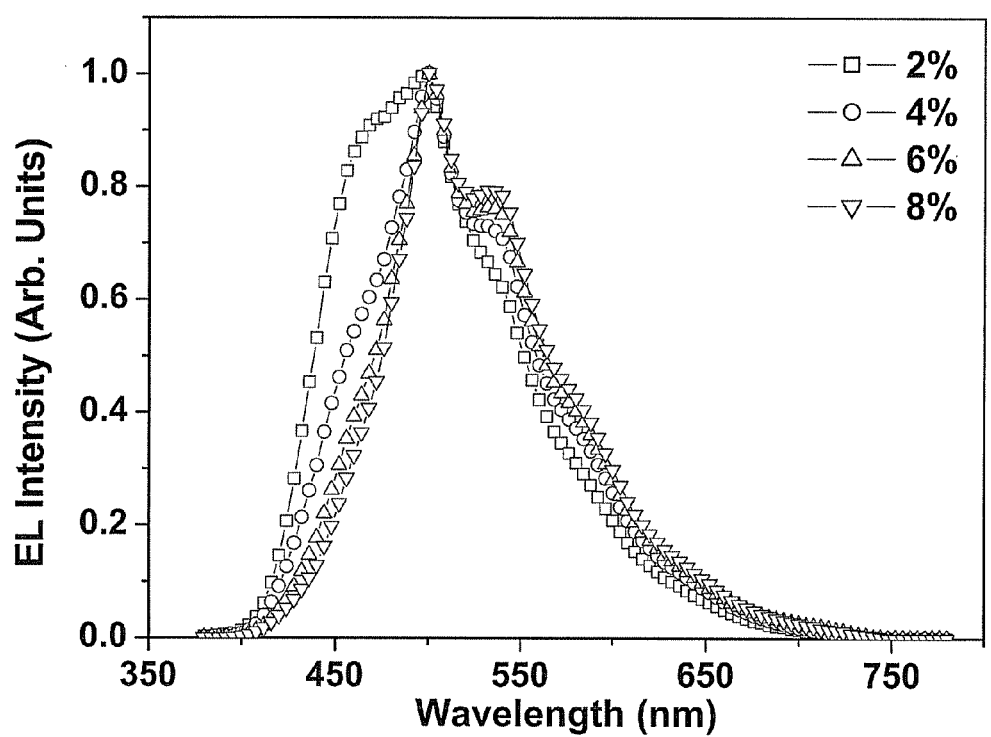
Figure 14: EL spectra for OLEDs 601-604

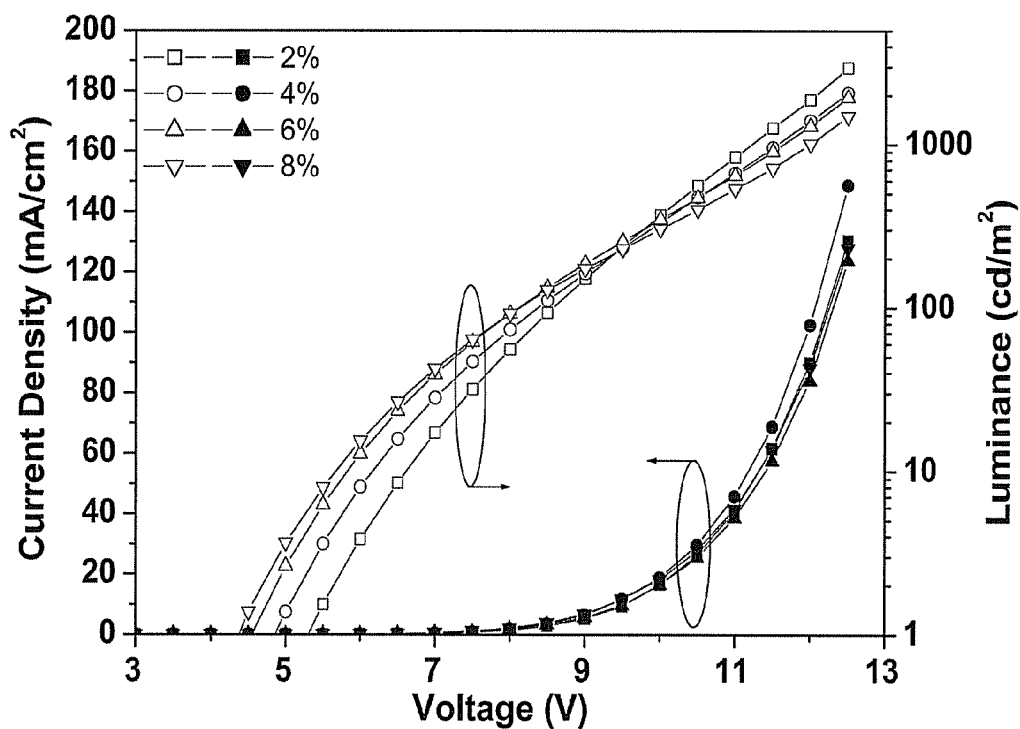
Figure 15: Current density-voltage-brightness (J-V-B) relationships for OLEDs 601-604

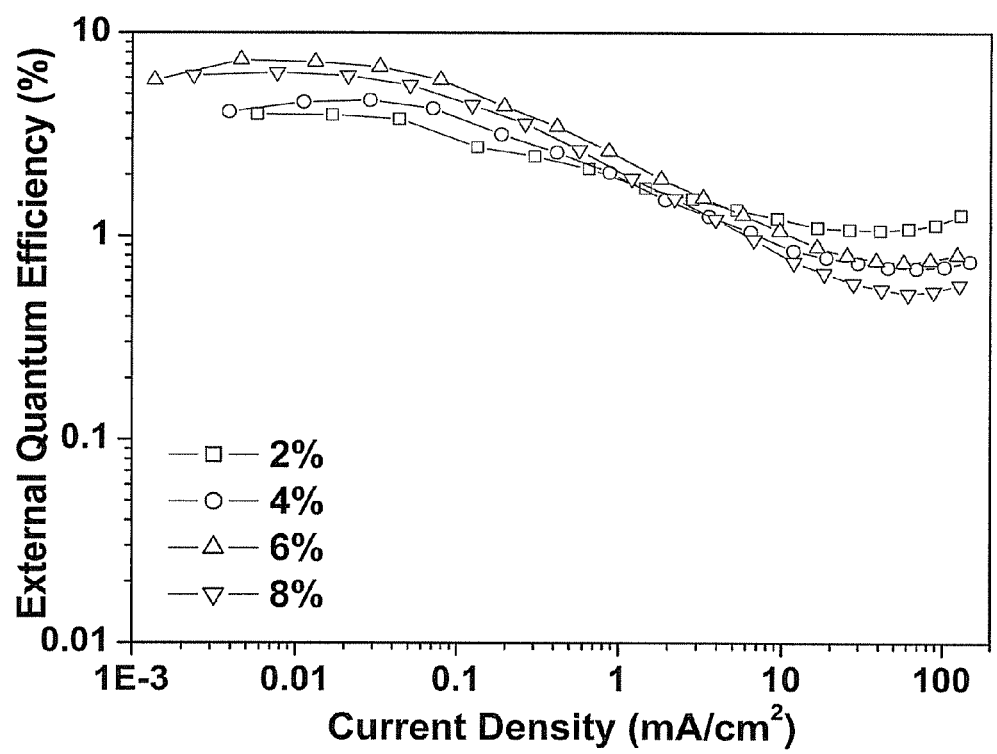
Figure 16: External quantum efficiency-current density relationships for OLEDs 601-604

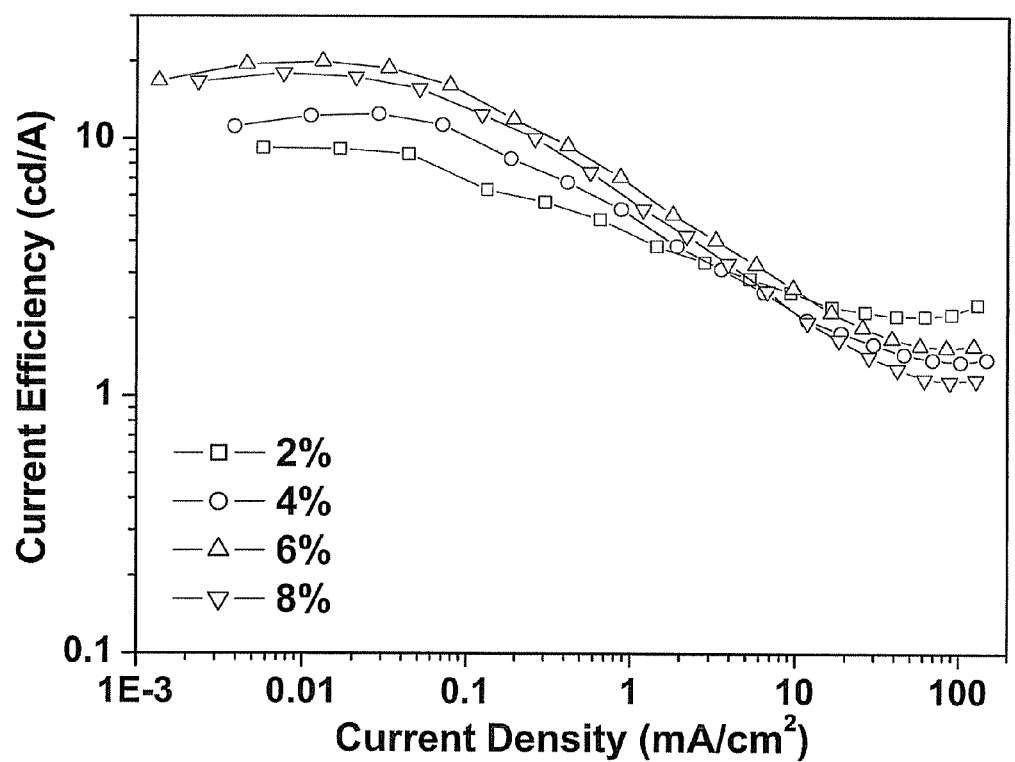
Figure 17: Current efficiency-current density relationships for OLEDs 601-604

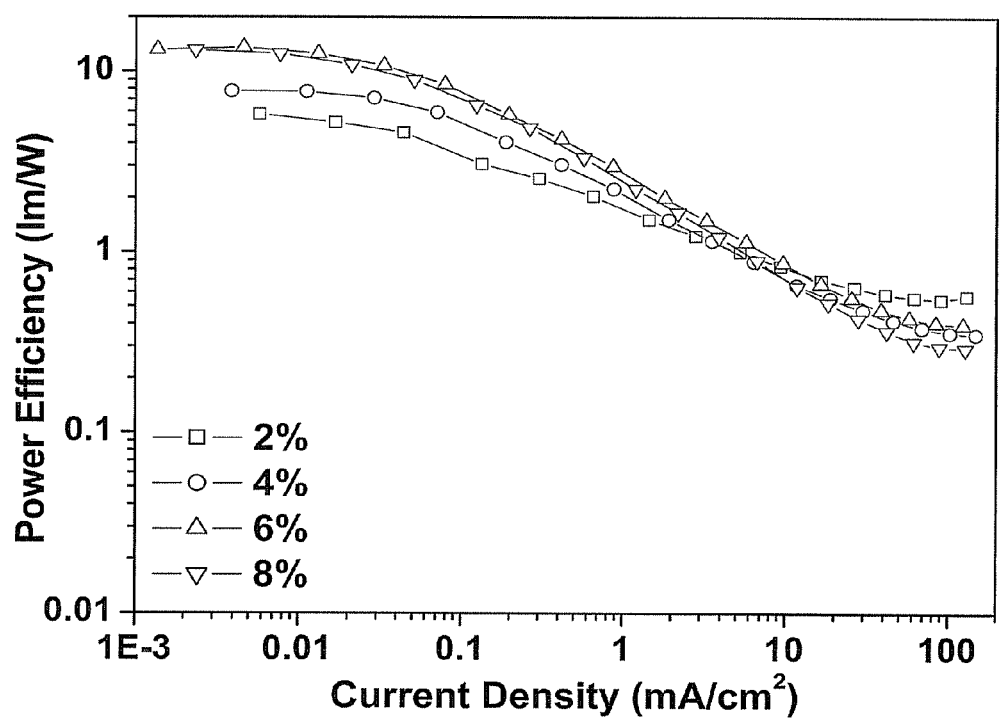
Figure 18: Power efficiency-current density relationships for OLEDs 601-604

PALLADIUM COMPLEXES FOR ORGANIC LIGHT-EMITTING DIODES

CROSS-REFERENCE TO RELATED APPLICATIONS

This application claims priority to provisional application Ser. No. 61/569,184, filed on Dec. 9, 2011, which is incorporated herein by reference.

TECHNICAL FIELD

Subject matter disclosed herein relates to a class of tetradentate palladium(II) complexes, their preparation method and their application in organic light-emitting diodes (OLED).

BACKGROUND

Organic light-emitting diodes (OLEDs) are recognized as a next-generation display and/or lighting technology. Due to the 3:1 triplet to singlet exciton issue, development of emitting materials for OLED application maybe mainly focused on phosphorescent materials. Among phosphorescent materials, metal organic materials containing heavy transition metals may exhibit desirable performance in OLED application. Iridium is a commonly used heavy transition metal while platinum is an up-and-coming candidate. Devices fabricated from iridium- and platinum-based materials have good device performance for mass production.

However, prices for iridium- and platinum-based materials may be relatively high. There is a desire to reduce costs for emitting materials. Zinc-based materials may provide an advantage related to cost, for example. Nevertheless, efficiency and/or stability of devices fabricated from zinc-based materials may be questionable.

SUMMARY

In various embodiments, phosphorescent materials, which can be used for OLED applications, comprise palladium as a metal center. One advantage associated with palladium over other materials is the relatively low price.

In various embodiments, palladium-based light-emitting materials comprise a molecular structure of Structure I:

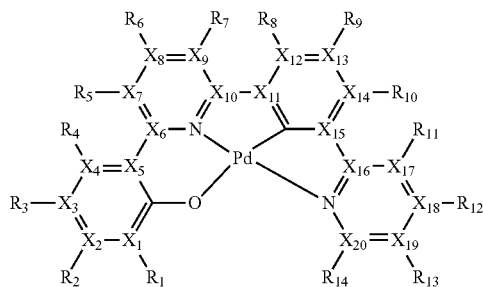

Structure I wherein $R_1$-$R_{14}$ are independently selected from hydrogen, halogen, oxygen, nitrogen, sulphur, selenium, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group, for example. Individual $R_1$-$R_{14}$ can independently form 5 to 8 member ring(s) with adjacent R group(s). The notation "$R_1$-$R_{14}$" means $R_1$, $R_2$, $R_3$, $R_4$ ... $R_{11}$, $R_{12}$, $R_{13}$, $R_{14}$, for example.

Individual $R_1$-$R_{14}$ can independently comprise the same atom(s) as an adjacent R group and form a 5 member ring with four X atoms to form a complex with a chemical structure of Structure II, for example. $X_1$-$X_{20}$ can be independently selected from boron, carbon, nitrogen, oxygen, or silicon, for example. The notation "$X_1$-$X_{20}$" means $X_1$, $X_2$, $X_3$, $X_4$ ... $X_{17}$, $X_{18}$, $X_{19}$, $X_{20}$, for example. Structure II is represented as:

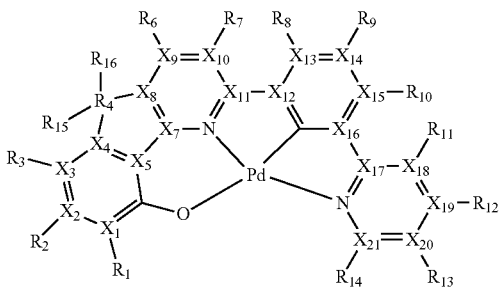

Structure II wherein $R_1$-$R_{14}$ are independently selected from hydrogen, halogen, oxygen, nitrogen, sulphur, selenium, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group and $X_1$-$X_{20}$ can be independently selected from boron, carbon, nitrogen, oxygen, or silicon.

BRIEF DESCRIPTION OF THE DRAWINGS

Non-limiting and non-exhaustive embodiments are described with reference to the following figures, wherein like reference numerals refer to like parts throughout the various figures unless otherwise specified.

FIG. 1 shows an x-ray crystal structure for illustrative complex 101, according to an embodiment.

FIG. 2 shows an x-ray crystal structure for illustrative complex 104, according to an embodiment.

FIG. 3 shows a UV-visible spectrum of illustrative complexes 101-103 in $CH_2Cl_2$ solution, according to an embodiment.

FIG. 4 shows a UV-visible spectrum of illustrative complexes 104-106 in $CH_2Cl_2$ solution, according to an embodiment.

FIG. 5 shows photoluminescent spectra of illustrative complexes 101-103 in $CH_2Cl_2$ solution, according to an embodiment.

FIG. 6 shows photoluminescent spectra of illustrative complexes 104-106 in $CH_2Cl_2$ solution, according to an embodiment.

FIG. 7 shows solid-state (298 K), solid-state (77 K) and glassy (77 K) photoluminescent spectra for Complex 101, according to an embodiment.

FIG. 8 shows solid-state (298 K), solid-state (77 K) and glassy (77 K) photoluminescent spectra for Complex 102, according to an embodiment.

FIG. 9 shows solid-state (298 K), solid-state (77 K) and glassy (77 K) photoluminescent spectra for Complex 10, according to an embodiment.

FIG. 10 shows solid-state (298 K), solid-state (77 K) and glassy (77 K) photoluminescent spectra for Complex 104, according to an embodiment.

FIG. 11 shows solid-state (298 K), solid-state (77 K) and glassy (77 K) photoluminescent spectra for Complex 105, according to an embodiment.

FIG. 12 shows solid-state (298 K), solid-state (77 K) and glassy (77 K) photoluminescent spectra for Complex 106, according to an embodiment.

FIG. 13 shows thermograms for illustrative complexes 104-106, according to an embodiment.

FIG. 14 shows EL spectra for OLEDs 601-604, according to an embodiment.

FIG. 15 shows current density-voltage-brightness (J-V-B) relationships for OLEDs 601-604, according to an embodiment.

FIG. 16 shows external quantum efficiency-current density relationships for OLEDs 601-604, according to an embodiment.

FIG. 17 shows current efficiency-current density relationships for OLEDs 601-604, according to an embodiment.

FIG. 18 shows power efficiency-current density relationships for OLEDs 601-604, according to an embodiment.

DETAILED DESCRIPTION

Palladium(II) typically has four coordinating sites. Consequently, five types of palladium(II) complexes are observable—$PdL_1L_2L_3L_4$; $PdL_1L_2L_5$; $PdL_5L_6$; $PdL_1L_7$; and $PdL_8$, where $L_1$-$L_4$ comprise monodentate ligands, which comprise the same ligand; $L_5$ and $L_6$ comprise bidentate ligands, $L_7$ comprises a tridentate ligand, and $L_8$ comprises a tetradentate ligand, for example. $PdL_8$-type complexes can have relatively strong binding between the ligand and the palladium center since four metal-ligand bonds are involved. Therefore, $PdL_8$-type complexes can have relatively high stability, and an OLED fabricated from $PdL_8$-type complexes can have relatively high stability and long lifetime. Since electronically neutral complexes can be more readily sublimated for thermal deposition OLED fabrication, a di-anionic ligand can be used for palladium(II) complexes for OLED applications, for example.

In an embodiment, an emissive palladium(II) complex system with a chemical structure of Structure I can be designed for an OLED application, Structure I represented as:

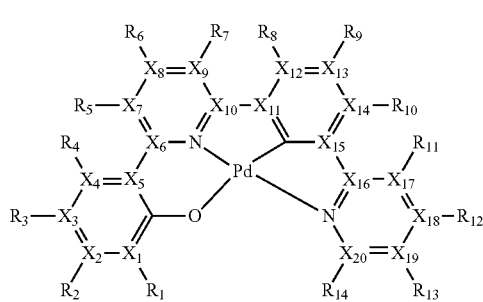

Structure I wherein $R_1$-$R_{14}$, if present, can be independently selected from hydrogen, halogen, oxygen, nitrogen, sulphur, selenium, hydroxyl, an unsubstituted alkyl having 1 to 14 carbon atoms, a substituted alkyl having 1 to 14 carbon atoms, cycloalkyl having 1 to 14 carbon atoms, an unsubstituted aryl having 1 to 14 carbon atoms, a substituted aryl having 1 to 14 carbon atoms, acyl having 1 to 14 carbon atoms, alkoxy having 1 to 14 carbon atoms, acyloxy having 1 to 14 carbon atoms, amino, nitro, acylamino having 1 to 14 carbon atoms, aralkyl having 1 to 14 carbon atoms, cyano, carboxyl, thio, styryl, aminocarbonyl, carbamoyl, aryloxycarbonyl, phenoxycarbonyl, or an alkoxycarbonyl group. Individual $R_1$-$R_{14}$ can also independently form 5 to 8 member ring(s) with adjacent R group(s). Individual $R_1$-$R_{14}$ can independently comprise the same atom(s) as the adjacent R group and form a 5 member ring with four X atoms to form a complex with a chemical structure of Structure II, for example. $X_1$-$X_{20}$ can be independently selected from boron, carbon, nitrogen, oxygen, or silicon, for example.

In another embodiment, in Structure I, each $R_1$-$R_{14}$ can be independently selected from hydrogen, halogen (such as fluorine, chlorine bromine, and iodine), hydroxyl, an unsubstituted alkyl including from 1 to 10 carbon atoms, a substituted alkyl including from 1 to 20 carbon atoms, cycloalkyl including from 1 to 20 carbon atoms, an unsubstituted aryl including from 1 to 20 carbon atoms, a substituted aryl including from 1 to 20 carbon atoms, acyl including from 1 to 20 carbon atoms, alkoxy including from 1 to 20 carbon atoms, acyloxy including from 1 to 20 carbon atoms, amino, nitro, acylamino including from 1 to 20 carbon atoms, aralkyl including from 1 to 20 carbon atoms, cyano, carboxyl including from 1 to 20 carbon atoms, thio, styryl, aminocarbonyl including from 1 to 20 carbon atoms, carbamoyl including from 1 to 20 carbon atoms, aryloxycarbonyl including from 1 to 20 carbon atoms, phenoxycarbonyl including from 1 to 20 carbon atoms, or an alkoxycarbonyl group including from 1 to 20 carbon atoms.

In another embodiment, a total number of carbon atoms provided by $R_1$-$R_{14}$ groups can be in a range from 1 to 40. In another embodiment, a total number of carbon atoms provided by $R_1$-$R_{14}$ groups can be in a range from 2 to 30.

In another embodiment, $R_4$=$R_5$=carbon atom to form a five member ring with four X atoms to form a complex with a chemical structure of Structure II,

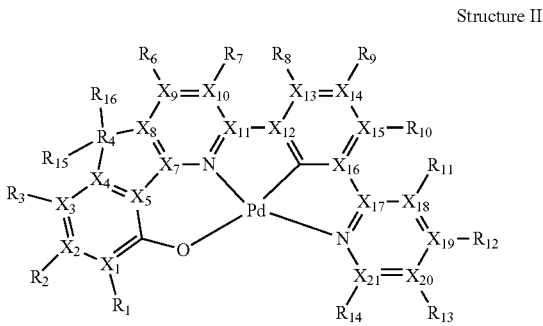

Structure II wherein $R_1$-$R_{14}$ groups and $X_1$-$X_{20}$ are as defined in Structure I and $R_{15}$-$R_{16}$ can be independently selected from hydrogen, halogen, hydroxyl, an unsubstituted alkyl including from 1 to 20 carbon atoms, a substituted alkyl including from 1 to 20 carbon atoms, cycloalkyl including from 1 to 20 carbon atoms, an unsubstituted aryl including from 1 to 20 carbon atoms, a substituted aryl including from 1 to 20 carbon atoms, acyl including from 1 to 20 carbon atoms, alkoxy including from 1 to 20 carbon atoms, acyloxy including from 1 to 20 carbon atoms, amino, nitro, acylamino including from 1 to 20 carbon atoms, aralkyl including from 1 to 20 carbon atoms, cyano, carboxyl, thio, styryl, aminocarbonyl, carbamoyl, aryloxycarbonyl, phenoxycarbonyl, or an alkoxycarbonyl group.

Some examples of palladium(II) complexes are shown below, though claimed subject matter is not so limited:

Complex 101

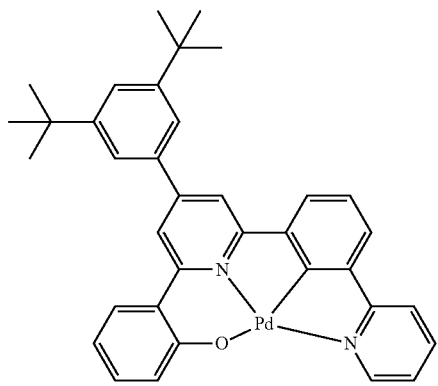

Complex 102

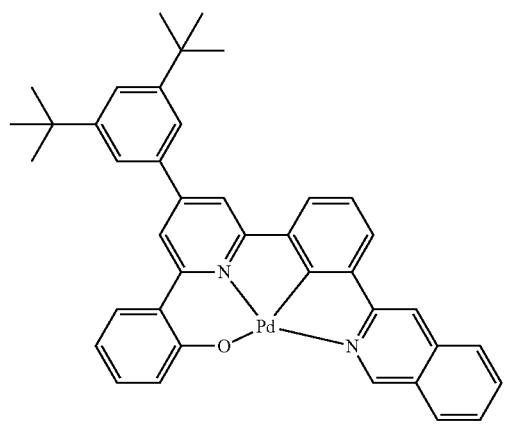

Complex 103

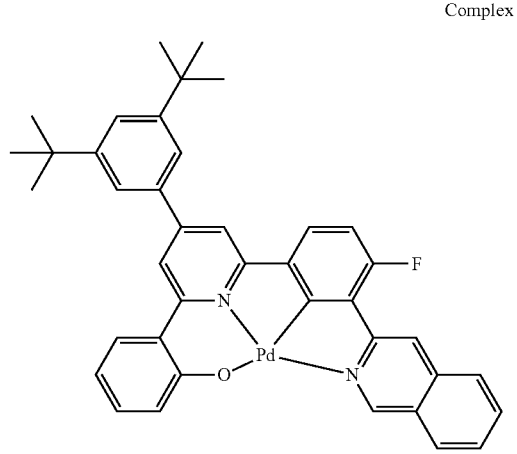

Complex 104

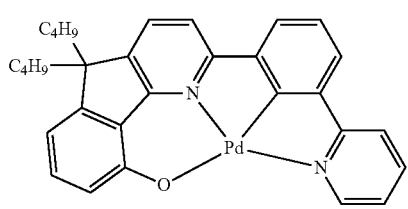

Complex 105

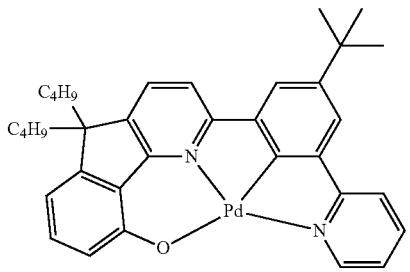

Complex 106

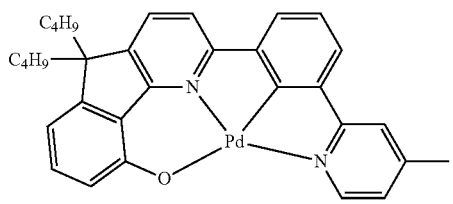

In an implementation, complexes such as those shown above can be prepared by reacting a palladium(II) salt with a corresponding protonated ligand in the presence of one or more suitable solvents. Examples of palladium(II) salts include but are not limited to palladium acetate, palladium chloride, dichloro(1,5-cyclooctadiene)platinum(II), and (ethylenediamine) palladium(II) chloride. Examples of solvents include but are not limited to glacial acetic acid, dichloromethane, chloroform, THF, DMF and DMSO, and mixtures thereof—refer to Reaction 201, for example. The product can then be optionally purified by column chromatography using alumina or silica as a stationary phase. Further purification by sublimation can be preformed if desired.

Reaction 201

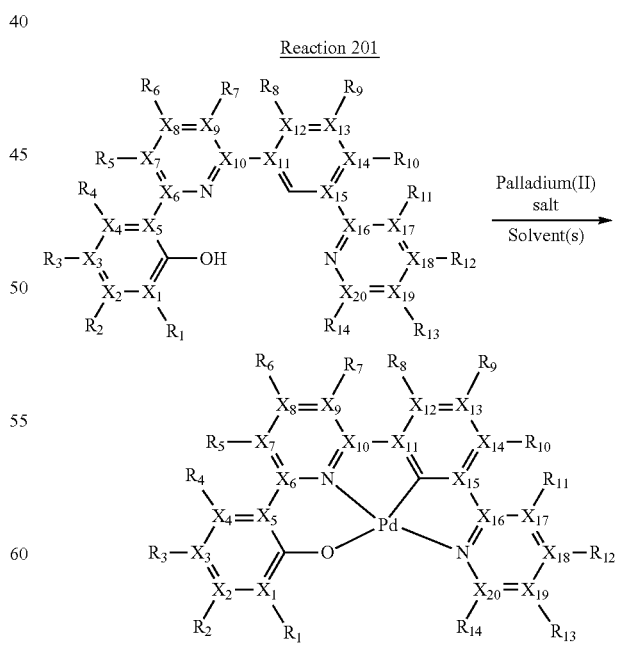

Some examples of protonated ligands are shown below, though claimed subject matter is not so limited:

Ligand 301

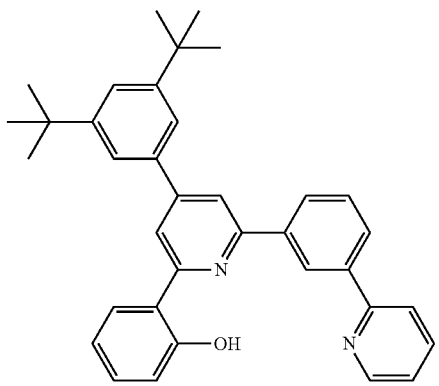

Ligand 302

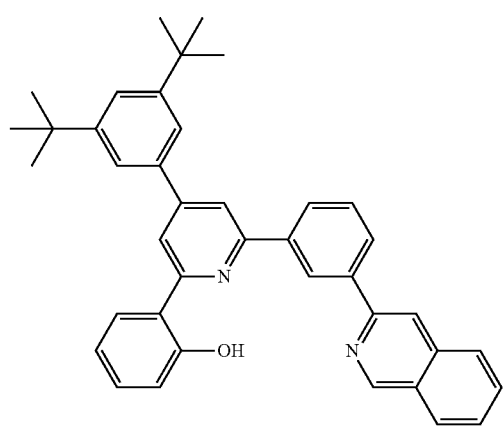

Ligand 303

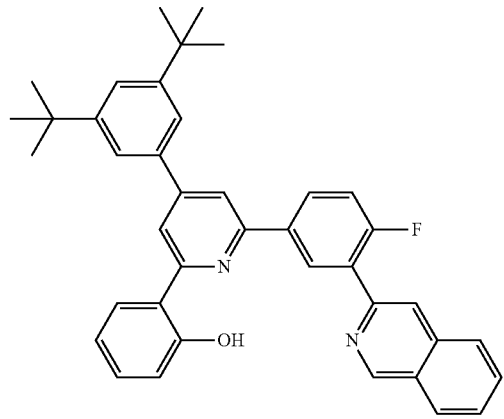

Ligand 304

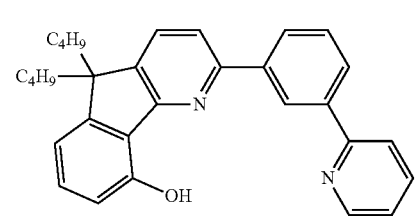

-continued

Ligand 305

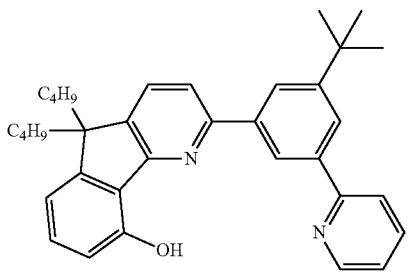

Ligand 306

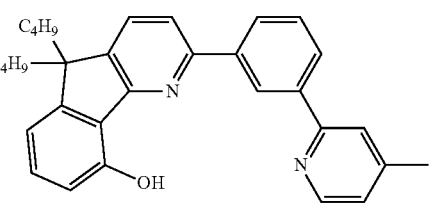

The following examples illustrate the subject invention. Unless otherwise indicated in the following examples and elsewhere in the specification and claims, all parts and percentages are by weight, all temperatures are in degrees Centigrade, and pressure is at or near atmospheric pressure.

Example 401

Synthesis of Complex 101

In one implementation, Ligand 301 (0.30 g, 0.59 mmol) was mixed with palladium acetate (0.14 g, 0.65 mmol) in glacial acetic acid (50 ml), and the reaction mixture was refluxed for 12 hr. The mixture was extracted with $CHCl_3$, and the organic layer was dried with $MgSO_4$. Purification was performed by alumina chromatography using chloroform as eluent to give Complex 101 as a yellow solid. Yield: 0.22 g (60%). $^1$H NMR (500 MHz, $CDCl_3$, 25° C., TMS): δ=1.44 (s, 18H), 6.67 (t, $^3$J (H, H)=8.0 Hz, 1H), 7.18-7.24 (m, 2H), 7.30-7.34 (m, 2H), 7.47 (d, $^3$J (H, H)=7.6 Hz, 1H), 7.56-7.57 (m, 3H), 7.61 (s, 1H), 7.70-7.72 (m, 2H), 7.90 (t, $^3$J (H, H)=7.8 Hz, 1H), 7.95 (d, $^3$J (H, H)=8.1 Hz, 1H), 8.18 (s, 1H), 8.86 (d, $^3$J (H, H)=4.7 Hz, 1H). FAB-MS (+ve, m/z): 616 $[M]^+$. An example, of the X-ray crystal structure of Complex 101 is depicted in FIG. 1, for example.

Example 402

Synthesis of Complex 102

Ligand 302 (0.30 g, 0.53 mmol) was mixed with palladium acetate (0.13 g, 0.59 mmol) in glacial acetic acid (50 ml), and the reaction mixture was refluxed for 12 hr. The mixture was extracted with $CHCl_3$, and the organic layer was dried with $MgSO_4$. Purification was performed by alumina chromatography using dichloromethane as eluent to give Complex 102 as yellow solid. Yield: 0.21 g (58%). $^1$H NMR (500 MHz, $CD_2Cl_2$, 25° C., TMS): δ=1.46 (s, 18H), 6.62 (ddd, $^4$J (H, H)=1.4 Hz, $^3$J (H, H)=6.6 Hz, $^3$J (H, H)=8.1 Hz, 1H), 7.15 (dd, $^4$J (H, H)=1.3 Hz, $^3$J (H, H)=8.4 Hz, 1H), 7.21 (t, $^3$J (H, H)=7.6 Hz, 1H), 7.29 (ddd, $^4$J (H, H)=1.7 Hz, $^3$J (H, H)=6.6 Hz, $^3$J (H, H)=8.4 Hz, 1H), 7.48 (d, $^3$J (H, H)=7.5 Hz, 1H), 7.52 (d, $^3$J (H, H)=7.5 Hz, 1H), 7.59-7.62 (m, 2H), 7.64 (t, $^4$J (H, H)=1.7 Hz, 1H), 7.67 (d, $^3$J (H, H)=1.6 Hz, 1H), 7.74 (dt, $^4$J (H, H)=1.1 Hz, $^3$J (H, H)=8.1 Hz, 1H), 7.81 (d, $^3$J (H, H)=8.1 Hz, 1H), 7.87 (s, 1H), 7.93 (dd, $^4$J (H, H)=1.5 Hz, $^3$J (H, H)=8.4 Hz, 1H), 8.04 (d, $^3$J (H, H)=8.1 Hz, 1H), 8.13 (d, $^4$J (H, H)=1.3 Hz, 1H), 9.35 (s, 1H). FAB-MS (+ve, m/z): 666 [M]$^+$.

Example 403

Synthesis of Complex 103

Ligand 303 (0.30 g, 0.52 mmol) was mixed with palladium acetate (0.13 g, 0.57 mmol) in glacial acetic acid (50 ml), and the reaction mixture was refluxed for 12 hr. The mixture was extracted with CHCl$_3$, and the organic layer was dried with MgSO$_4$. Purification was performed by alumina chromatography using chloroform as eluent to give Complex 103 as pale yellow solid. Yield: 0.26 g (65%). $^1$H NMR (500 MHz, CD$_2$Cl$_2$, 25° C.): δ=1.45 (s, 18H), 6.59 (ddd, $^4$J (H, H)=1.4 Hz, $^3$J (H, H)=6.7 Hz, $^3$J (H, H) 8.2 Hz, 1H), 6.85 (dd, $^3$J (H, H)=8.3 Hz, $^3$J (F, H)=11.6 Hz, 1H), 7.11 (dd, $^4$J (H, H)=1.4 Hz, $^3$J (H, H)=8.4 Hz, 1H), 7.26 (ddd, $^4$J (H, H)=1.7 Hz, $^3$J (H, H)=6.7 Hz, $^3$J (H, H)=8.4 Hz, 1H), 7.47 (dd, $^4$J (F, H)=3.8 Hz, $^3$J (H, H) 8.4 Hz, 1H), 7.57 (d, $^4$J (H, H)=1.6 Hz, 1H), 7.60 (d, $^4$J (H, H)=1.8 Hz, 1H), 7.63-7.68 (m, 2H), 7.80 (dt, $^4$J (H, H)=1.1 Hz, $^3$J (H, H)=8.1 Hz, 1H), 7.84 (d, $^3$J (H, H)=8.0 Hz, 1H), 7.88 (dd, $^4$J (H, H)=1.5 Hz, $^3$J (H, H)=8.4 Hz, 1H), 8.06-8.08 (m, 2H), 8.12 (s, 1H), 9.38 (s, 1H). FAB-MS (+ve, m/z): 684 [M]$_+$.

Example 404

Synthesis of Complex 104

Ligand 304 (0.30 g, 0.67 mmol) was mixed with palladium acetate (0.17 g, 0.74 mmol) in glacial acetic acid (50 ml), and the reaction mixture was refluxed for 12 hr. The mixture was extracted with CHCl$_3$, and the organic layer may be dried with MgSO$_4$. Purification was performed by alumina chromatography using dichloromethane as eluent to give Complex 104 as yellow solid. Yield: 0.22 g (60%). $^1$H NMR (500 MHz, CD$_2$Cl$_2$, 25° C., TMS): δ=0.68-0.82 (m, 10H), 1.09-1.17 (m, 4H), 1.95-2.08 (m, 4H), 6.60 (d, J=7.1 Hz, 1H), 6.90 (d, J=8.4 Hz, 1H), 7.25 (t, J=7.7 Hz, 1H), 7.36-7.29 (m, 2H), 7.50-7.53 (m, 2H), 7.59 (d, J=7.6 Hz, 1H), 7.79-7.81 (m, 2H), 7.95 (dt, J$_{1,2}$=1.6 Hz, J$_{1,3}$=7.8 Hz, 1H), 8.84-8.85 (m, 1H). FAB-MS (+ve, m/z): 552 [M]$^+$. An example, of the x-ray crystal structure of Complex 104 is depicted in FIG. 2.

Example 405

Synthesis of Complex 105

Ligand 305 (0.30 g, 0.59 mmol) was mixed with palladium acetate (0.15 g, 0.65 mmol) in glacial acetic acid (50 ml), and the reaction mixture was refluxed for 12 hr. The mixture was extracted with CHCl$_3$, and the organic layer may be dried with MgSO$_4$. Purification was performed by alumina chromatography using dichloromethane as eluent to give Complex 105 as pale yellow solid. Yield: 0.22 g (60%). $^1$H NMR (500 MHz, CD$_2$Cl$_2$, 25° C., TMS): δ=0.68-0.79 (m, 10H), 1.09-1.16 (m, 4H), 1.95-2.08 (m, 4H), 6.58 (d, $^3$J (H, H)=7.0 Hz, 1H), 6.88 (d, $^3$J (H, H)=8.3 Hz, 1H), 7.34-7.39 (m, 2H), 7.54 (d, $^3$J (H, H)=7.6 Hz, 1H), 7.62 (d, $^4$J (H, H)=1.6 Hz, 1H), 7.68 (d, $^4$J (H, H)=1.6 Hz, 1H), 7.80 (d, $^3$J (H, H)=7.6 Hz, 1H), 7.85 (d, $^3$J (H, H)=7.9 Hz, 1H), 7.96-7.99 (m, 1H), 8.82-8.84 (m, 1H). FAB-MS (+ve, m/z): 608 [M]$^+$.

Example 406

Synthesis of Complex 106

Ligand 306 (0.25 g, 0.54 mmol) was mixed with palladium acetate (0.13 g, 0.59 mmol) in glacial acetic acid (50 ml), and the reaction mixture was refluxed for 12 hr. The mixture was extracted with CHCl$_3$, and the organic layer may be dried with MgSO$_4$. Purification was performed by alumina chromatography using dichloromethane as eluent to give Complex 106 as yellow solid. Yield: 0.17 g (55%). $^1$H NMR (500 MHz, CD$_2$Cl$_2$, 25° C., TMS): δ=0.68-0.80 (m, 10H), 1.09-1.16 (m, 4H), 1.95-2.08 (m, 4H), 2.52 (s, 3H), 6.59 (d, $^3$J (H, H)=6.8 Hz, 1H), 6.88 (d, $^3$J (H, H)=8.2 Hz, 1H), 7.20-7.21 (m, 1H), 7.25 (t, $^3$J (H, H)=7.7 Hz, 1H), 7.36 (dd, $^3$J (H, H)=7.1 Hz, $^3$J (H, H)=8.4 Hz, 1H), 7.49-7.53 (m, 2H), 7.59 (d, $^3$J (H, H)=6.9 Hz, 1H), 7.64 (s, 1H), 7.80 (d, $^3$J (H, H)=7.6 Hz, 1H), 8.67 (d, $^3$J (H, H)=5.6 Hz, 1H). FAB-MS (+ve, m/z): 567 [M]$^+$.

Example 407

Photophysical Data for Complexes 101-106

The absorption spectra of complexes 101-103 (an example of which is depicted in FIG. 3) show relatively intense transitions with $\lambda_{max}$ ranging from 250-340 nm, which can be assigned to be intraligand transitions with mainly ligand character, while the transitions ranging from 340-400 nm can be assigned to be metal perturbed intraligand transitions (with considerable metal character). Relatively broad absorption at about 400-470 nm (ϵ≈5000-11000 dm$^3$ mol$^{-1}$ cm$^{-1}$) for complexes 101-103 can be attributed to a $^1$MLCT (5d)Pt→π*(L) transition, although mixing with IL may not be excluded. These assignments can be supported by a solvent effect experiment on complex 101. Upon or after forming UV spectra, with an increase in solvent polarity, blue shifts of ~8 nm and ~13 nm in regions of 340-400 nm and 400-470 nm, respectively, can be recorded to show metal involvement in excited states, for example.

Absorption spectra of complexes 104-106 (an example of which is depicted in FIG. 4) show relatively intense transitions with $\lambda_{max}$ ranging from 250-320 nm, which can be assigned to comprise intraligand transitions having substantially ligand character, while transitions ranging from 320-400 nm can be assigned to comprise metal perturbed intraligand transitions having considerable metal character. Broad absorption at 400-470 nm (ϵ≈7200-7700 dm$^3$ mol$^{-1}$ cm$^{-1}$) for complexes 104-106 can be attributed to $^1$MLCT (5d)Pt→π* (L) transition, although mixing with IL need not be excluded. These assignments can be supported by a solvent effect experiment on complex 105. Upon or after forming UV spectra, with an increase in solvent polarity, blue shifts of ~6 nm in the regions of 320-400 nm and 400-470 nm can be recorded to show metal involvement in excited states, for example.

Complexes 101-103 can be emissive in degassed CH$_2$Cl$_2$. Emission energy listed in descending order: Complex 103>Complex 101>Complex 102, which can be due to an effect of fluorine substituent (e.g., lowers the HOMO energy) and extension of pyridine to isoquinoline (e.g., lowers the LUMO energy). For complexes 101-103, their emission spectra may not be vibronically resolved (an example of which is depicted in FIG. 5), and emission energy need not be affected by a concentration ranging from 1×10$^{-4}$ M to 1×10$^{-5}$ M. Thus their emissions can originate from an excited state of $^3$ILCT (e.g., lone pair on oxygen atom to other parts of the ligand) mixed with $^3$MLCT, tentatively. These assignments can be supported by a solvent effect experiment on complex 101. Upon or after forming emission spectra, with an increase in solvent polarity, red shifts of ~20 nm can be recorded, which can be a characteristic behaviour of $^3$ILCT.

Complexes 104-106 can be highly emissive in degassed $CH_2Cl_2$. Their emission energy, which can be similar, can mean that alkyl substituents may not affect emission energy. And their emission spectra can be vibronically resolved (an example of which is depicted in FIG. 6), which can possess vibronic spacings of 1200 cm$^{-1}$ and emission energy may not be affected from the concentration ranging from 1×10$^-$ M to 1×10$^{-5}$ M, for example. Thus their emissions can be assigned to come from an excited state of $^3$IL, and the mixing of $^3$MLCT may not be excluded. These assignments can be supported by the solvent effect experiment on Complex 105. Upon or after forming emission spectra, with an increase in solvent polarity, emission energy can be similar, which can be a characteristic behaviour for an emission from $^3$IL.

Emission quantum yields of complexes 101-103 (Φ≈0.0018-0.0030) can be lower than that of complexes 104-106 (Φ≈0.11-0.20), which can reveal that complexes 104-106 can possess more rigid structures and can reduce excited state distortions. For solid state emission at room temperature, all complexes except complex 104, can show excimeric emissions due, at least in part, to serious aggregations. Complex 104 can show a structured emission with $\lambda_{max}$ of 500 nm. Such emission can be attributed to originate from $^3$IL excited state. On cooling to 77 K, emission spectra of complexes 101-104 can show vibronic structures with vibronic spacings of 1300-1400 cm$^{-1}$ (an example of which is depict in FIG. 7-FIG. 10), which may correspond to vibration frequency of C=C and C=N, and the $\lambda_{max}$ may be in a range from 529 to 557 nm. These emissions can be attributed to come from $^3$IL excited states, for example. Emission spectra of complex 105 and complex 106 narrowed down upon cooling may still be affected by serious aggregations. Such emission specta can comprise mainly excimeric emissions. Glassy solution (2-MeTHF) of complexes 101-106 can show vibronic structured emissions with vibronic spacings of 1300-1400 cm$^{-1}$, which can correspond to a vibrational frequency of C=C and C=N (an example of which is depicted in FIG. 11-FIG. 12). The $\lambda_{max}$ of complexes 101-103 can vary from 477 to 505 nm, while that of complexes 104-106 can be almost the same at ~488 nm.

In one embodiment, the term "relatively narrow color emission spectrum" refers to a spectrum that is 30 or fewer nanometers wide, such as that of a "single" color spectrum, for example. In another embodiment, the term "relatively narrow color emission spectrum" refers to a spectrum that is 20 or fewer nanometers wide. In yet another embodiment, the term "relatively narrow color emission spectrum" refers to a spectrum that is 10 or fewer nanometers wide. Of course, a relatively narrow color emission spectrum can be wider or narrower, and claimed subject matter is not limited in this respect.

TABLE 501

Physical properties of illustrative Complexes 101-106.

| Complexes | Medium (T/K) | λabs/nm$^{a,b}$ (ε/× 10$^4$ dm$^3$ mol$^{-1}$ cm$^{-1}$) | λem/nm$^c$ (τ/μs); | Φem$^d$ |
|---|---|---|---|---|
| 101 | $CH_2Cl_2$ (298) | 246 (7.15), 283 (8.54), 358 (2.53), 415 (1.14) | 538 | 0.002 |
|  | Solid (298) | — | 434 (0.31), 571 (0.32), 650 (0.57) | — |
|  | Solid (77) | — | 539 (62.3), 549 (66.9), 576 (61.5) | — |
|  | 2-MeTHF (77) | — | 477 (274), 502 (287), 513 (305), 545 (292), 554 (296), 585 (296) | — |
| 102 | $CH_2Cl_2$ (298) | 267 (5.92), 280 (6.46), 306 (4.17), 357 (2.06), 386 (1.13), 407 (0.63) | 543 (0.18) | 0.003 |
|  | Solid (298) | — | 426 (0.16), 526 (0.24), 575 (0.27) | — |
|  | Solid (77) | — | 552 (153), 578 (148) | — |
|  | 2-MeTHF (77) | — | 504 (2761), 519 (2883), 545 (2816), 587 (2659), 638 (3008) | — |
| 103 | $CH_2Cl_2$ (298) | 240 (5.01), 281 (6.33), 300 (4.16), 354 (1.74), 367 (1.34), 410 (0.50) | 535 (0.22) | 0.0018 |
|  | Solid (298) | — | 525 (0.28), 615 (0.35), 663 (0.24) | — |
|  | Solid (77) | — | 491 (3.48), 556 (101), 594 (65.79) | — |
|  | 2-MeTHF (77) | — | 493 (3309), 509 (3313), 534 (3351), 576 (3593), 624 (3679) | — |
| 104 | $CH_2Cl_2$ (298) | 252 (4.23), 270 (3.06), 345 (1.44), 372 (1.20), 409 (0.64) | 527 (82) | 0.110 |
|  | Solid (298) | — | 483 (0.55), 500 (0.68), 536 (0.43) | — |

TABLE 501-continued

Physical properties of illustrative Complexes 101-106.

| Complexes | Medium (T/K) | $\lambda abs/nm^{a,b}$ ($\epsilon$/x $10^4$ $dm^3$ $mol^{-1}$ $cm^{-1}$) | $\lambda em/nm^c$ ($\tau/\mu s$); | $\Phi em^d$ |
|---|---|---|---|---|
| | Solid (77) | — | 458 (0.22), 500 (6.11), 530 (591), 558 (553) | — |
| | 2-MeTHF (77) | — | 487 (775), 517 (809), 526 (846), 563 (828), 601 (832) | — |
| 105 | $CH_2Cl_2$ (298) | 253 (4.82), 272 (3.36), 295 (2.01), 347 (1.46), 379 (1.33), 407 (0.79) | 498 (121) | 0.200 |
| | Solid (298) | — | 497 (1.39), 537 (4.03), 554 (4.08), 576 (4.10) | — |
| | Solid (77) | — | 490 (4.93), 535 (643), 549 (693) | — |
| | 2-MeTHF (77) | — | 486 (749), 524 (742), 564 (735), 604 (747) | — |
| 106 | $CH_2Cl_2$ (298) | 252 (4.85), 269 (3.69), 347 (1.64), 372 (1.34), 405 (0.81) | 527 (122) | 0.170 |
| | Solid (298) | — | 498 (0.60), 542 (0.68), 568 (0.62) | — |
| | Solid (77) | — | 451 (0.52), 500 (4.60), 515 (5.10), 541 (10.16), 554 (8.55), 567 (7.12), 585 (6.18), 732 (1.11) | — |
| | 2-MeTHF (77) | — | 487 (771), 506 (837), 515 (832), 526 (832), 561 (835), 571 (845), 601 (841) | — |

[a]Absorption maxima.
[b]at 2 × $10^{-5}$ M.
[c]Emission maxima.
[d]Emission Quantum Yield.

Example 408

Thermal Behaviour for Complexes 101-106

Thermal behaviour of some illustrative materials can be measured using thermogravimetric analyses (TGA) at a heating rate of 40° C. $min^{-1}$, for example. Some examples of thermograms are depicted in FIG. 13. TGA can measure weight changes in a material as a function of temperature (or time) under a controlled atmosphere. Complexes 101-106 may possess relatively high thermal stability and can be stable to air and moisture. Decomposition temperature ($T_d$) of complexes 101-106 can range from 414 to 468° C., as shown in Table 502.

TABLE 502

Decomposition temperature for 101-106.

| Complex | Decomposition Temperature/° C. |
|---|---|
| 101 | 450 |
| 102 | 468 |
| 103 | 444 |
| 104 | 421 |
| 105 | 418 |
| 106 | 414 |

Example 409

OLED Fabrication

In some embodiments, OLEDs can be prepared on patterned indium tin oxide (ITO). Pre-coated glass slides with a sheet resistance of 10 $\Omega/m^2$ can be used as anodic substrates, for example. The glass slides can be cleaned with Decon 90 detergent, rinsed in de-ionized water, and dried in an oven before successive film deposition. Glass slides can then be treated in an ultraviolet-ozone chamber before loading into an evaporation chamber. Layers of organic material and metal can be thermally deposited sequentially in a high vacuum evaporator (such as that manufactured by Trovato Mfg., Inc., Fairport, N.Y., for example) with a base pressure of $10^{-6}$ Torr. Films can be sequentially deposited at a rate of 0.1-0.2 nm/s without vacuum break. Film thicknesses can be determined in-situ by calibrated oscillating quartz-crystal sensors. Shadow masks can be used to define organic layers and a cathode may be used to make, for example, four 0.1 $cm^2$ devices on each substrate. The Commission Internationale de L'Eclairage (CIE) coordinates, current density-voltage-luminance characteristics (J-V-L), and electroluminescence (EL) spectra were measured (at different times or at the same time) with a programmable Keithley model 2400 source-meter measurement unit and a Photoresearch PR-655 spectrascan spectroradiometer. All experiments and measurements can be performed at room temperature under ambient environment without device encapsulation, though claimed subject matter is not so limited.

OLEDs 601-604 were prepared in the following configuration: ITO/NPB (40 nm)/mCP: Complex 5, X %, 30 nm)/BAlq$_3$ (40 nm)/LiF (0.5 nm)/Al (80 nm), wherein OLED 601 (X=2%), OLED 602 (X=4%), OLED 603 (X=6%) and OLED 604 (X=8%). These devices were CIE coordinates of: OLED 601: 0.22, 0.32; OLED 602: 0.25, 0.40; OLED 603: 0.27, 0.44; OLED 604: 0.28, 0.47. The EL $\lambda_{max}$ (500, 530 nm with a shoulder at ~580 nm) can be independent of doping concentrations for complex 105. Turn on voltages of OLED 601-604 are 5.3 V, 4.9 V, 4.6 V, and 4.4 V, respectively. For OLED 601, an upper current efficiency of 9.2 cd A$^{-1}$ was obtained at 0.006 mA cm$^{-2}$. An upper power efficiency (PE) and an upper external quantum efficiency (EQE) were 5.7 lmW$^1$ and 4.0%, respectively. For OLED 602, an upper current efficiency of 12.5 cd A$^{-1}$ was obtained at 0.029 mA cm$^{-2}$. An upper power efficiency (PE) and an upper external quantum efficiency (EQE) were 7.8 lmW$^1$ and 4.7%, respectively. For OLED 603, an upper current efficiency of 20.0 cd A$^{-1}$ was obtained at 0.013 mA cm$^{-2}$. An upper power efficiency (PE) and an upper external quantum efficiency (EQE) were 13.6 lmW$^1$ and 7.4%, respectively. For OLED 604, an upper current efficiency of 18.0 cd A$^{-1}$ was obtained at 0.008 mA cm$^{-2}$. An upper power efficiency (PE) and an upper external quantum efficiency (EQE) were 13.1 lmW$^{-1}$ and 6.4%, respectively. FIG. 16, FIG. 17, and FIG. 18 show examples of an EL spectrum, J-V-B curves, external quantum efficiency, current efficiency, and power efficiency as a function of drive current density for OLEDs 601-604, respectively.

Some examples of EL spectra, J-V-B relationships, and efficiency curves for OLEDs 601-604 are depicted in FIG. 13, FIG. 14, and FIG. 15, respectively.

With respect to any figure or numerical range for a given characteristic, a figure or a parameter from one range may be combined with another figure or a parameter from a different range for the same characteristic to generate a numerical range.

Other than in the operating examples, or where otherwise indicated, all numbers, values and/or expressions referring to quantities of ingredients, reaction conditions, etc., used in the specification and claims are to be understood as modified in all instances by the term "about."

While there has been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter may also include all aspects falling within the scope of appended claims, and equivalents thereof.

What is claimed is:

1. An organometallic complex having a chemical structure of Structure I:

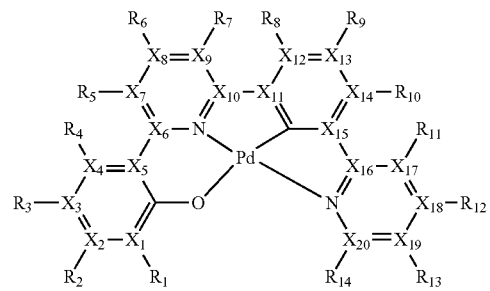

Structure I wherein each $R_1$-$R_{14}$ is independently selected from hydrogen, halogen, hydroxyl, an unsubstituted alkyl including from 1 to 10 carbon atoms, a substituted alkyl including from 1 to 20 carbon atoms, cycloalkyl including from 1 to 20 carbon atoms, an unsubstituted aryl including from 1 to 20 carbon atoms, a substituted aryl including from 1 to 20 carbon atoms, acyl including from 1 to 20 carbon atoms, alkoxy including from 1 to 20 carbon atoms, acyloxy including from 1 to 20 carbon atoms, amino, nitro, acylamino including from 1 to 20 carbon atoms, aralkyl including from 1 to 20 carbon atoms, cyano, carboxyl including from 1 to 20 carbon atoms, thio, styryl, aminocarbonyl including from 1 to 20 carbon atoms, carbamoyl including from 1 to 20 carbon atoms, aryloxycarbonyl including from 1 to 20 carbon atoms, phenoxycarbonyl including from 1 to 20 carbon atoms, or an alkoxycarbonyl group including from 1 to 20 carbon atoms, and wherein each $X_1$-$X_{20}$ is independently selected from the group consisting of boron, carbon, nitrogen, oxygen, and silicon.

2. The organometallic complex of claim 1, wherein the individual $R_1$-$R_{14}$ groups independently form 5 to 8 member rings with adjacent R groups.

3. The organometallic complex of claim 2, wherein the individual $R_1$-$R_{14}$ independently comprise a same atom as an adjacent R groups.

4. The organometallic complex of claim 1, wherein the individual $R_1$-$R_{14}$ form a 5 member ring with four of the X atoms to form a complex having a chemical structure of Structure II:

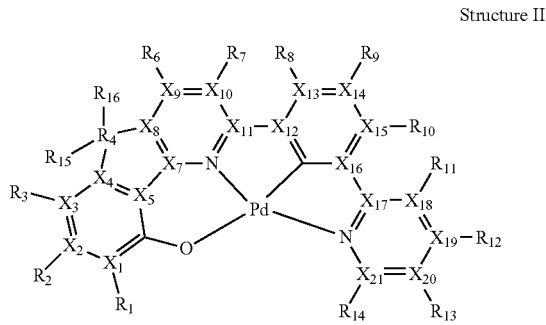

Structure II wherein $R_1$-$R_{14}$ groups and $X_1$-$X_{20}$ are as defined in Structure I and each of $R_{15}$-$R_{16}$ is independently selected from hydrogen, halogen, hydroxyl, an unsubstituted alkyl including from 1 to 20 carbon atoms, a substituted alkyl including from 1 to 20 carbon atoms, cycloalkyl including from 1 to 20 carbon atoms, an unsubstituted aryl including from 1 to 20 carbon atoms, a substituted aryl including from 1 to 20 carbon atoms, acyl including from 1 to 20 carbon atoms, alkoxy including from 1 to 20 carbon atoms, acyloxy including from 1 to 20 carbon atoms, amino, nitro, acylamino including from 1 to 20 carbon atoms, aralkyl including from 1 to 20 carbon atoms, cyano, carboxyl, thio, styryl, aminocarbonyl, carbamoyl, aryloxycarbonyl, phenoxycarbonyl, or an alkoxycarbonyl group.

5. The organometallic complex of claim 1, further comprising one of Complex 101, Complex 102, Complex 103, Complex 104, Complex 105, and Complex 106 as follows:

Complex 101

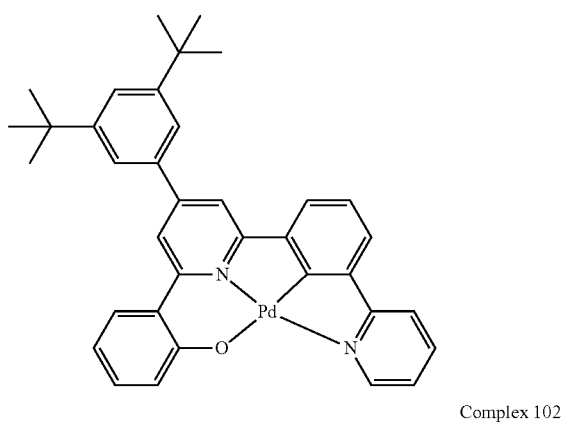

Complex 102

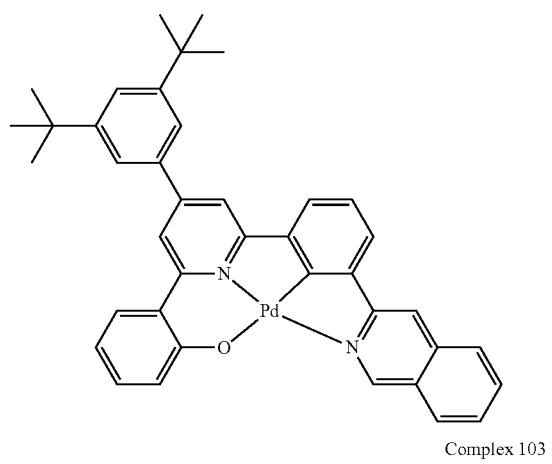

Complex 103

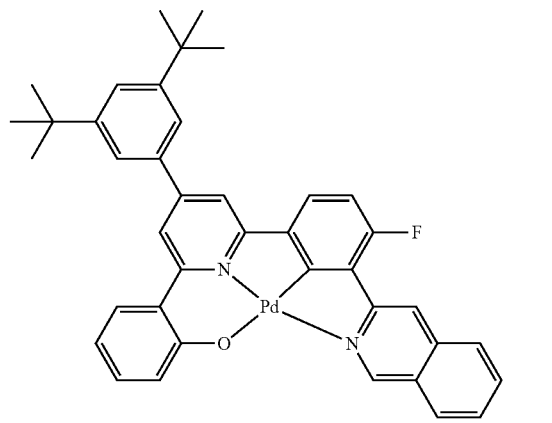

Complex 104

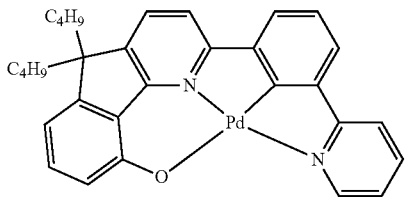

Complex 105

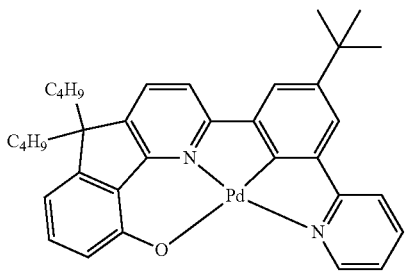

Complex 106

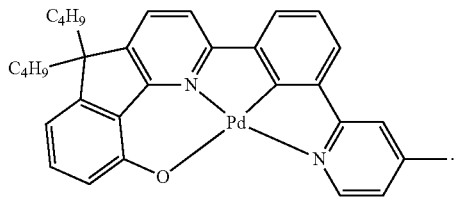

6. The organometallic complex of claim 1, wherein the organometallic complex is incorporated in an organic light-emitting diode (OLED).

7. The organometallic complex of claim 1, wherein the organometallic complex is incorporated in a polymer light-emitting diode (PLED).

8. The organometallic complex of claim 6, wherein the OLED is fabricated by thermal deposition.

9. The organometallic complex of claim 6, wherein the OLED is fabricated by spin coating.

10. The organometallic complex of claim 6, wherein the OLED is fabricated by printing.

11. The organometallic complex of claim 7, wherein the PLED is fabricated by spin coating.

12. The organometallic complex of claim 7, wherein the PLED is fabricated by printing.

13. The organometallic complex of claim 8, wherein the OLED emits a relatively narrow color emission spectrum originating from the organometallic complex.

14. The organometallic complex of claim 11, wherein the PLED emits a relatively narrow color emission spectrum originating from the organometallic complex.

15. The organometallic complex of claim 8, wherein the OLED emits a white emission comprising an emission from the organometallic complex and one or more different emission components from other emitting materials.

16. The organometallic complex of claim 11, wherein the PLED emits a white emission comprising an emission from said organometallic complex and one or more different emission components from other emitting materials.

17. A method of preparing an organometallic complex, comprising:

producing a chemical structure of Structure I,

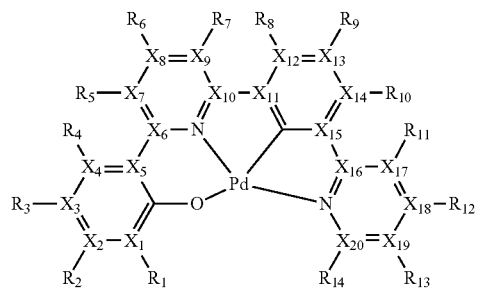

Structure I wherein each $R_1$-$R_{14}$ is independently selected from hydrogen, halogen, hydroxyl, an unsubstituted alkyl including from 1 to 10 carbon atoms, a substituted alkyl including from 1 to 20 carbon atoms, cycloalkyl including from 1 to 20 carbon atoms, an unsubstituted aryl including from 1 to 20 carbon atoms, a substituted aryl including from 1 to 20 carbon atoms, acyl including from 1 to 20 carbon atoms, alkoxy including from 1 to 20 carbon atoms, acyloxy including from 1 to 20 carbon atoms, amino, nitro, acylamino including from 1 to 20 carbon atoms, aralkyl including from 1 to 20 carbon atoms, cyano, carboxyl including from 1 to 20 carbon atoms, thio, styryl, aminocarbonyl including from 1 to 20 carbon atoms, carbamoyl including from 1 to 20 carbon atoms, aryloxycarbonyl including from 1 to 20 carbon atoms, phenoxycarbonyl including from 1 to 20 carbon atoms, or an alkoxycarbonyl group including from 1 to 20 carbon atoms, and wherein each $X_1$-$X_{20}$ is independently selected from the group consisting of boron, carbon, nitrogen, oxygen, and silicon.

18. The method of claim 17, wherein the individual $R_1$-$R_{14}$ groups form 5 to 8 member rings with adjacent R groups.

19. The method of claim 18, wherein the individual $R_1$-$R_{14}$ comprise a same atom as an adjacent R group.

20. The method of claim 18, wherein the individual $R_1$-$R_{14}$ form a 5 member ring with four of said $X_1$-$X_{20}$ atoms to form a complex with a chemical structure of Structure II:

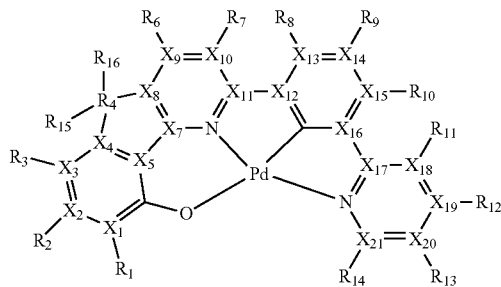

Structure II wherein $R_1$-$R_{14}$ groups and $X_1$-$X_{20}$ are as defined in Structure I and each of $R_{15}$-$R_{16}$ is independently selected from hydrogen, halogen, hydroxyl, an unsubstituted alkyl including from 1 to 20 carbon atoms, a substituted alkyl including from 1 to 20 carbon atoms, cycloalkyl including from 1 to 20 carbon atoms, an unsubstituted aryl including from 1 to 20 carbon atoms, a substituted aryl including from 1 to 20 carbon atoms, acyl including from 1 to 20 carbon atoms, alkoxy including from 1 to 20 carbon atoms, acyloxy including from 1 to 20 carbon atoms, amino, nitro, acylamino including from 1 to 20 carbon atoms, aralkyl including from 1 to 20 carbon atoms, cyano, carboxyl, thio, styryl, aminocarbonyl, carbamoyl, aryloxycarbonyl, phenoxycarbonyl, or an alkoxycarbonyl group.

* * * * *